United States Patent [19]

Andree et al.

[11] Patent Number: 6,008,160
[45] Date of Patent: Dec. 28, 1999

[54] SUBSTITUTED 1-AMINO-3-PHENYLURACIL DERIVATIVES, THEIR PREPARATION AND THEIR USE AS HERBICIDES

[75] Inventors: Roland Andree; Mark Wilhelm Drewes, both of Langenfeld; Markus Dollinger, Leverkusen, all of Germany

[73] Assignee: Bayer Aktiengesellschaft, Leverkusen, Germany

[21] Appl. No.: 09/029,212

[22] PCT Filed: Aug. 22, 1996

[86] PCT No.: PCT/EP96/03693

§ 371 Date: Feb. 25, 1998

§ 102(e) Date: Feb. 25, 1998

[87] PCT Pub. No.: WO97/09319

PCT Pub. Date: Mar. 13, 1997

[30] Foreign Application Priority Data

Sep. 4, 1995 [DE] Germany .................. 195 32 344

[51] Int. Cl.[6] .................. A01N 43/54; C07D 239/02; C07D 239/00; C07D 239/54
[52] U.S. Cl. .................. 504/243; 544/242; 544/298; 544/309; 544/311; 544/312; 504/242
[58] Field of Search .................. 544/311, 312; 504/242, 243

[56] References Cited

U.S. PATENT DOCUMENTS

| | | | |
|---|---|---|---|
| 5,116,404 | 5/1992 | Ishii et al. | 71/92 |
| 5,593,945 | 1/1997 | Andree et al. | 504/243 |
| 5,681,794 | 10/1997 | Andree et al. | 504/243 |

FOREIGN PATENT DOCUMENTS

| | | |
|---|---|---|
| 0 420 194 | 4/1991 | European Pat. Off. . |
| 0 438 209 | 7/1991 | European Pat. Off. . |
| 0 517 181 | 12/1992 | European Pat. Off. . |
| 0 540 023 | 5/1993 | European Pat. Off. . |
| 0 563 384 | 10/1993 | European Pat. Off. . |
| 0 648 749 | 4/1995 | European Pat. Off. . |
| 22 07 549 | 8/1973 | Germany . |
| 24 41 156 | 3/1976 | Germany . |
| WO 95 29168 | 11/1995 | WIPO . |

Primary Examiner—S. Mark Clardy
Assistant Examiner—Sabiha N. Qazi
Attorney, Agent, or Firm—Sprung Kramer Schaefer & Briscoe

[57] ABSTRACT

The invention relates to novel substituted aminouracils of the general formula (I)

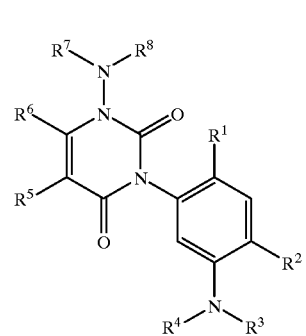

(I)

in which $R^1$, $R^2$, $R^3$, $R^4$, $R^5$, $R^6$, $R^7$ and $R^8$ are each as defined in the claims, to the preparation thereof and to their use as herbicides.

4 Claims, No Drawings

SUBSTITUTED 1-AMINO-3-PHENYLURACIL DERIVATIVES, THEIR PREPARATION AND THEIR USE AS HERBICIDES

The invention relates to novel substituted aminouracils, to the preparation thereof and to their use as herbicides.

Certain substituted uracils are known to have herbicidal properties (cf. EP 408382/U.S. Pat. No. 5,084,084/U.S. Pat. No. 5,127,935/U.S. Pat. No. 5,154,755/EP 563384/EP 648749/WO 91/00278/U.S. Pat. No. 4,979,982/U.S. Pat. No. 5,169,430). However, these compounds are of no particular importance.

This invention, accordingly, provides the novel substituted aminouracils of the general formula (I)

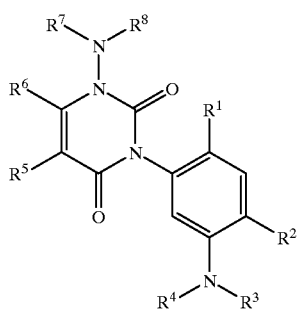

(I)

in which $R^1$ represents hydrogen, cyano or halogen, $R^2$ represents cyano or thiocarbamoyl, $R^3$ represents hydrogen or represents a respectively optionally substituted radical from the group consisting of alkyl, alkylcarbonyl, alkenyl, alkenylcarbonyl, alkinyl, alkinylcarbonyl, cycloalkyl, cycloalkylcarbonyl, cycloalkylalkyl, cycloalkylalkylcarbonyl, arylcarbonyl, arylalkylcarbonyl and heterocyclylcarbonyl, $R^4$ represents hydrogen or represents a respectively optionally substituted radical from the group consisting of alkyl, alkylcarbonyl, alkenyl, alkenylcarbonyl, alkinyl, alkinylcarbonyl, cycloalkyl, cycloalkylcarbonyl, cycloalkylalkyl, cycloalkylalkylcarbonyl, arylcarbonyl, arylalkylcarbonyl and heterocyclylcarbonyl, or together with $R^3$ represents respectively optionally substituted alkanediyl, oxoalkanediyl or dioxoalkanediyl, $R^5$ represents hydrogen, halogen or respectively optionally substituted alkyl or alkoxy, $R^6$ represents optionally substituted alkyl, $R^7$ represents hydrogen or represents a respectively optionally substituted radical from the group consisting of alkyl, alkenyl and alkinyl, and $R^8$ represents hydrogen or represents a respectively optionally substituted radical from the group consisting of alkyl, alkenyl and alkinyl.

The novel substituted aminouracils of the general formula (I) are obtained when aminouracils of the general formula (II)

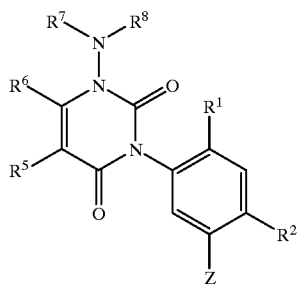

(II)

in which $R^1$, $R^2$, $R^5$, $R^6$, $R^7$ and $R^8$ are each as defined above and Z represents optionally substituted alkylsulphonylamino or the grouping $NR^3R^4$, where $R^3$ and $R^4$ are each as defined above, are reacted with alkylating or acylating agents of the general formulae (III), (IV), (V) or (VI)

$$X—R^3 \quad (III)$$

$$R^3—CO—O—CO—R^3 \quad (IV)$$

$$X—R^4 \quad (V)$$

$$R^4—CO—O—CO—R^4 \quad (VI)$$

in which $R^3$ and $R^4$ are each as defined above, if appropriate in the presence of a reaction auxiliary and if appropriate in the presence of a diluent.

The compounds of the general formula (I) can be converted by conventional methods into other compounds of the general formula (I) according to the definition above, for example by deacylation with ammonium acetate/glacial acetic acid ($R^3/R^4$: —CO—CH$_3$→H) or by the addition of hydrogen sulphide ($R^2$: CN→CSNH$_2$).

The novel substituted aminouracils of the general formula (I) have strong herbicidal properties.

In the definitions, the saturated or unsaturated hydrocarbon chains, such as alkyl, alkenyl or alkinyl, are in each case straight-chain or branched.

Halogen generally represents fluorine, chlorine, bromine or iodine, preferably fluorine, chlorine or bromine, in particular fluorine or chlorine.

The invention preferably provides compounds of the formula (I) in which $R^1$ represents hydrogen, cyano, fluorine or chlorine, $R^2$ represents cyano or thiocarbamoyl, $R^3$ represents hydrogen or represents respectively optionally cyano-, carboxyl-, fluorine-, chlorine-, bromine-, $C_1$–$C_4$-alkoxy-, $C_1$–$C_4$-alkyl-carbonyl- or $C_1$–$C_4$-alkoxy-carbonyl-substituted alkyl, alkylcarbonyl, alkenyl, alkenylcarbonyl, alkinyl or alkinylcarbonyl having in each case up to 10 carbon atoms in the alkyl, alkenyl or alkinyl moieties, $R^3$ furthermore represents respectively optionally cyano-, carboxyl-, fluorine-, chlorine-, bromine-, $C_1$–$C_4$-alkyl-, $C_1$–$C_4$-alkoxy-, $C_1$–$C_4$-alkyl-carbonyl- or $C_1$–$C_4$-alkoxy-carbonyl-substituted cycloalkyl, cycloalkylcarbonyl, cycloalkylalkyl or cycloalkylalkylcarbonyl having in each case 3 to 8 carbon atoms in the cycloalkyl moiety and optionally up to 4 carbon atoms in the alkyl moiety, $R^3$ furthermore represents arylcarbonyl or arylalkylcarbonyl having 6 or 10 carbon atoms in the aryl moiety and optionally up to 4 carbon atoms in the alkyl moiety, each of the arylcarbonyl or arylalkylcarbonyl radicals optionally being substituted by cyano, carboxyl, nitro, carbamoyl, thiocarbamoyl, fluorine, chlorine, bromine, by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl or $C_1$–$C_4$-alkoxy-carbonyl (each of which is optionally substituted by fluorine and/or chlorine), by phenyl, phenoxy or phenylthio (each of which is optionally substituted by fluorine, chlorine, bromine, cyano, methyl, methoxy, trifluoromethyl and/or trifluoromethoxy), $R^3$ furthermore represents substituted furylcarbonyl, tetrahydrofurylcarbonyl, thienylcarbonyl, tetrahydrothienylcarbonyl, oxazolylcarbonyl, isoxazolylcarbonyl, thiazolylcarbonyl, oxadiazolylcarbonyl, thiadiazolylcarbonyl, pyrazolylcarbonyl, pyridinylcarbonyl or pyrimidinylcarbonyl, each of which is optionally substituted by cyano, carboxyl, carbamoyl, thiocarbamoyl, fluorine, chlorine, bromine, by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl or $C_1$–$C_4$-alkoxy-carbonyl (each of which is optionally substituted by fluorine and/or chlorine), by phenyl, phenoxy or phenylthio (each of which is optionally substituted by fluorine, chlorine, bromine, cyano, methyl, methoxy, trifluoromethyl and/or trifluoromethoxy), $R^4$ represents hydrogen or represents respectively optionally cyano-, carboxyl-, fluorine-, chlorine-, bromine-, $C_1$–$C_4$-alkoxy-, $C_1$–$C_4$-alkyl-carbonyl- or $C_1$–$C_4$-alkoxy-carbonyl-substituted alkyl, alkylcarbonyl, alkenyl, alkenylcarbonyl, alkinyl or alkinylcarbonyl having in each case up to 10 carbon atoms in the alkyl, alkenyl or alkinyl moieties, $R^4$ furthermore represents respectively optionally cyano-, carboxyl-, fluorine-, chlorine-, bromine-, $C_1$–$C_4$-alkyl-, $C_1$–$C_4$-alkoxy-, $C_1$–$C_4$-alkyl-carbonyl- or $C_1$–$C_4$-alkoxy-carbonyl-substituted cycloalkyl, cycloalkylcarbonyl, cycloalkylalkyl or cycloalkylalkylcarbonyl having in each case 3 to 8 carbon atoms in the cycloalkyl moiety and optionally up to 4 carbon atoms in the alkyl moiety, $R^4$ furthermore represents arylcarbonyl or arylalkylcarbonyl having 6 or 10 carbon atoms in the aryl moiety and optionally up to 4 carbon atoms in the alkyl moiety, each of the arylcarbonyl or arylalkylcarbonyl radicals optionally being substituted by cyano, carboxyl, nitro, carbamoyl, thiocarbamoyl, fluorine, chlorine, bromine, by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl or $C_1$–$C_4$-alkoxy-carbonyl (each of which is optionally substituted by fluorine and/or chlorine), by phenyl, phenoxy or phenylthio (each of which is optionally substituted by fluorine, chlorine, bromine, cyano, methyl, methoxy, trifluoromethyl and/or trifluoromethoxy), $R^4$ furthermore represents furylcarbonyl, tetrahydrofurylcarbonyl, thienylcarbonyl, tetrahydrothienylcarbonyl, oxazolylcarbonyl, isoxazolylcarbonyl, thiazolylcarbonyl, oxadiazolylcarbonyl, thiadiazolylcarbonyl, pyrazolylcarbonyl, pyridinylcarbonyl or pyrimidinylcarbonyl, each of which is optionally substituted by cyano, carboxyl, carbamoyl, thiocarbamoyl, fluorine, chlorine, bromine, by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl or $C_1$–$C_4$-alkoxy-carbonyl (each of which is optionally substituted by fluorine and/or chlorine), by phenyl, phenoxy or phenylthio (each of which is optionally substituted by fluorine, chlorine, bromine, cyano, methyl, methoxy, trifluoromethyl and/or trifluoromethoxy), $R^4$ together with $R^3$ represents respectively optionally fluorine-, chlorine-, bromine-, $C_1$–$C_4$-alkyl- or $C_1$–$C_4$-halogenoalkyl-substituted alkanediyl, oxoalkanediyl or dioxoalkanediyl having in each case up to 6 carbon atoms, $R^5$ represents hydrogen, fluorine, chlorine, bromine or represents respectively optionally fluorine- and/or chlorine-substituted alkyl or alkoxy having in each case 1 to 4 carbon atoms, $R^6$ represents optionally fluorine- and/or chlorine-substituted alkyl having 1 to 4 carbon atoms, $R^7$ represents hydrogen or represents respectively optionally fluorine-, chlorine- or $C_1$–$C_4$-alkoxy-substituted alkyl, alkenyl or alkinyl having in each case up to 6 carbon atoms, and $R^8$ represents hydrogen or represents respectively optionally fluorine-, chlorine- or $C_1$–$C_4$-alkoxy-substituted alkyl, alkenyl or alkinyl having in each case up to 6 carbon atoms.

The invention in particular provides compounds of the formula (I) in which $R^1$ represents hydrogen, fluorine or chlorine, $R^2$ represents cyano or thiocarbamoyl, $R^3$ represents hydrogen or represents respectively optionally cyano-, carboxyl-, fluorine-, chlorine-, methoxy-, ethoxy-, n- or i-propoxy-, acetyl-, propionyl-, methoxycarbonyl-, ethoxycarbonyl-, n- or i-propoxycarbonyl-substituted methyl, ethyl, n- or i-propyl, n-, i-, s- or t-butyl, n-, i-, s- or t-pentyl, acetyl, n- or i-propyl-carbonyl, n-, i-, s- or t-butyl-carbonyl, propenyl, propenylcarbonyl, butenyl, butenylcarbonyl, pentenyl, pentenylcarbonyl, propinyl, propinylcarbonyl, butinyl, butinylcarbonyl, pentinyl or pentinylcarbonyl, $R^3$ furthermore represents respectively optionally cyano-, carboxyl-, fluorine-, chlorine-, bromine-, methyl-, ethyl-, n- or i-propyl-, methoxy-, ethoxy-, n- or i-propoxy-, acetyl- or propionyl-, methoxycarbonyl-, ethoxycarbonyl-, n- or i-propoxycarbonyl-substituted cyclopropyl, cyclopropylcarbonyl, cyclobutyl, cyclobutylcarbonyl, cyclopentyl, cyclopentylcarbonyl, cyclohexyl, cyclohexylcarbonyl, cyclopropylmethyl, cyclobutylmethyl, cyclopentylmethyl or cyclohexylmethyl, $R^3$ furthermore represents respectively optionally cyano-, carboxyl-, nitro-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, methylthio-, ethylthio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-substituted phenylcarbonyl, phenylmethylcarbonyl or phenylethylcarbonyl, $R^3$ furthermore represents respectively optionally cyano-, carboxyl-, carbamoyl-, thiocarbamoyl-, fluorine-, chlorine-, bromine-, methyl-, ethyl-, n- or i-propyl-, methoxy-, ethoxy-, n- or i-propoxy-, methylthio-, ethylthio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-, phenyl-, phenoxy- or phenylthio-substituted substituted furylcarbonyl, tetrahydrofurylcarbonyl, thienylcarbonyl, tetrahydrothienylcarbonyl, oxazolylcarbonyl, isoxazolylcarbonyl, thiazolylcarbonyl, oxadiazolylcarbonyl, thiadiazolylcarbonyl, pyrazolylcarbonyl, pyridinylcarbonyl or pyrimidinylcarbonyl, $R^4$ represents hydrogen or represents respectively optionally cyano-, carboxyl-, fluorine-, chlorine-, methoxy-, ethoxy-, n- or i-propoxy-, acetyl-, propionyl-, methoxycarbonyl-, ethoxycarbonyl-, n- or i-propoxycarbonyl-substituted methyl, ethyl, n- or i-propyl, n-, i-, s- or t-butyl, n-, i-, s- or t-pentyl, acetyl, n- or i-propyl-carbonyl, n-, i-, s- or t-butyl-carbonyl, propenyl, propenylcarbonyl, butenyl, butenylcarbonyl, pentenyl, pentenylcarbonyl, propinyl, propinylcarbonyl, butinyl, butinylcarbonyl, pentinyl or pentinylcarbonyl, $R^4$ furthermore represents respectively optionally cyano-, carboxyl-, fluorine-, chlorine-, bromine-, methyl-, ethyl-, n- or i-propyl-, methoxy-, ethoxy-, n- or i-propoxy-, acetyl- or propionyl-, methoxycarbonyl-, ethoxycarbonyl-, n- or i-propoxycarbonyl-substituted cyclopropyl, cyclopropylcarbonyl, cyclobutyl, cyclobutylcarbonyl, cyclopentyl, cyclopentylcarbonyl, cyclohexyl, cyclohexylcarbonyl, cyclopropylmethyl, cyclobutylmethyl, cyclopentylmethyl or cyclohexylmethyl, $R^4$ furthermore represents respectively optionally cyano-, carboxyl-, nitro-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, methylthio-, ethylthio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-substituted phenylcarbonyl, phenylmethylcarbonyl or phenylethylcarbonyl, $R^4$ furthermore represents respectively optionally cyano-, carboxyl-, carbamoyl-, thiocarbamoyl-, fluorine-, chlorine-, bromine-, methyl-, ethyl-, n- or i-propyl-, methoxy-, ethoxy-, n- or i-propoxy-, methylthio-, ethylthio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-, phenyl-, phenoxy- or phenylthio-substituted furylcarbonyl, tetrahydrofurylcarbonyl, thienylcarbonyl, tetrahydrothienylcarbonyl, oxazolylcarbonyl, isoxazolylcarbonyl, thiazolylcarbonyl, oxadiazolylcarbonyl, thiadiazolylcarbonyl, pyrazolylcarbonyl, pyridinylcarbonyl or pyrimidinylcarbonyl, or $R^4$ together with $R^3$ represents respectively optionally fluorine-, chlorine-, methyl- or trifluoromethyl-substituted propane-1,3-diyl (trimethylene), butane-1,4-diyl (tetramethylene), 1-oxo-propane- 1,3-diyl, 1-oxo-butane-1,4-diyl, 1,3-dioxopropane-1,3-diyl or 1,4-dioxobutane-1,4-diyl, $R^5$ represents hydrogen, fluorine, chlorine, bromine or methyl, $R^6$ represents methyl, ethyl, difluoromethyl, dichloromethyl, trifluoromethyl, trichloromethyl, chlorodifluoromethyl, fluorodichloromethyl, chloroethyl, fluoroethyl, dichloroethyl, dichloroethyl, chlorofluoroethyl, chlorodifluoroethyl, fluorodichloroethyl, trifluoroethyl, tetrafluoroethyl, chlorotrifluoroethyl or pentafluoroethyl, $R^7$ represents hydrogen or represents respectively optionally fluorine-, chlorine-, methoxy- or ethoxy-substituted methyl ethyl, n- or i-propyl, n-, i-, s- or t-butyl, methoxy, ethoxy, n- or i-propoxy, n-, i- or s- butoxy, propenyl, butenyl, propinyl or butinyl, and $R^8$ represents hydrogen or represents respectively optionally fluorine-, chlorine-methoxy- or ethoxy-substituted methyl, ethyl, n- or i-propyl, n-, i-, s- or t-butyl, methoxy, ethoxy, n- or i-propoxy, n-, i- or s- butoxy, propenyl, butenyl, propinyl or butinyl.

The radical definitions listed above, whether general or listed in ranges of preference, apply not only to the end products of formula (I) but also, correspondingly, to the starting materials and/or intermediates required in each case for the preparation. These radical definitions can be combined as desired with one another, thus including combinations between the preferred ranges indicated.

Examples of compounds of the formula (I) according to the invention are listed in the groups below.

Group 1

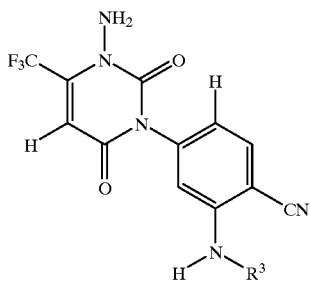

$R^3$ has, for example, the meanings given in the list below: hydrogen, methyl, ethyl, n- or i-propyl, n-, i-, s- or t-butyl, n-, i-, s- or t-pentyl, acetyl, n- or i-propyl-carbonyl, n-, i-, s- or t-butyl-carbonyl, n-, i-, s- or t-pentyl-carbonyl, difluoroacetyl, trifluoroacetyl, chlorodifluoroacetyl, fluorodichloroacetyl, fluoroprionyl, chloropropionyl, chlorofluoropropionyl, difluoropropionyl, dichloropropionyl, trifluoropropionyl, trichloropropionyl, chlorodifluoropropionyl, tetrafluoropropionyl, chlorotrifluoropropionyl, pentafluoropropionyl, fluorobutyroyl, chlorobutyroyl, difluorobutyroyl, dichlorobutyroyl, trifluorobutyroyl, cyanomethyl, cyanoacetyl, cyanoethyl, cyanopropionyl, cyanopropyl, cyanobutyroyl, carboxymethyl, carboxyethyl, carboxypropyl, carboxybutyl, methoxymethyl, methoxyacetyl, ethoxymethyl, ethoxyacetyl, propoxymethyl, propoxyacetyl, methoxyethyl, methoxypropionyl, ethoxyethyl, propoxyethyl, methoxypropyl, methoxybutyroyl, ethoxypropyl, ethoxybutyroyl, methoxycarbonylmethyl, ethoxycarbonylmethyl, propoxycarbonylmethyl, methoxycarbonylethyl, ethoxycarbonylethyl, propoxycarbonylethyl, methoxycarbonylpropyl, ethoxycarbonylpropyl, 1-propen-3-yl (allyl), 3-methyl-1-propen-3-yl, 2-buten-4-yl (crotonyl), 1-propin-3-yl (propargyl), 3-methyl-1-propin-3-yl, 2-butin-4-yl, cyclopropyl, cyclopropylcarbonyl, cyanocyclopropyl, carboxycyclopropyl, difluorocyclopropyl, dichlorocyclopropyl, methylcyclopropyl, methoxycarbonylcyclopropyl, ethoxycarbonylcyclopropyl, cyclobutyl, cyclobutylcarbonyl, cyanocyclobutyl, carboxycyclobutyl, difluorocyclobutyl difluorocyclobutylcarbonyl, trifluorocyclobutyl, trifluorocyclobutylcarbonyl, tetrafluorocyclobutyl, tetrafluorocyclobutylcarbonyl, chlorotrifluorocyclobutyl, chlorotrifluorocyclobutylcarbonyl, methylcyclobutyl, cyclopentyl, cyclopentylcarbonyl, cyanocyclopentyl, carboxycyclopentyl, fluorocyclopentyl, chiorocyclopentyl, difluorocyclopentyl, dichlorocyclopentyl, methylcyclopentyl, methoxycarbonylcyclopentyl, ethoxycarbonylcyclopentyl, cyclohexyl, cyclohexylcarbonyl, cyanocyclohexyl, carboxycyclohexyl, fluorocyclohexyl, chlorocyclohexyl, difluorocyclohexyl, dichlorocyclohexyl, methylcyclohexyl, trifluoromethylcyclohexyl, methoxycarbonylcyclohexyl, ethoxycarbonylcyclohexyl, cyclopropylmethyl, difluorocyclopropylmethyl, dichlorocyclopropylmethyl, cyclobutylmethyl, cyclopentylmethyl, cyclohexylmethyl, cyanocyclohexylmethyl, carboxycyclohexylmethyl, fluorocyclohexylmethyl, chlorocyclo-hexylmethyl, methylcyclohexylmethyl, trifluoromethylcyclohexylmethyl, benzoyl, cyanobenzoyl, nitrobenzoyl, fluorobenzoyl, chlorobenzoyl, bromobenzoyl, methylbenzoyl, trifluoromethylbenzoyl, methoxybenzoyl, difluoromethoxybenzoyl, trifluoromethoxybenzoyl, phenylacetyl, furylcarbonyl, tetrahydrofurylcarbonyl, thienylcarbonyl, tetrahydrothienylcarbonyl, oxazolylcarbonyl, isoxazolylcarbonyl, pyridylcarbonyl.

Group 2

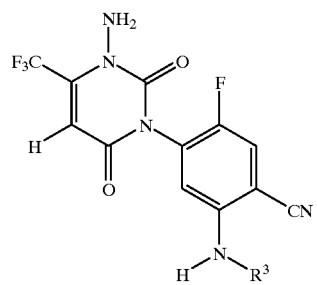

$R^3$ has, for example, the meanings given above for Group 1.

Group 3

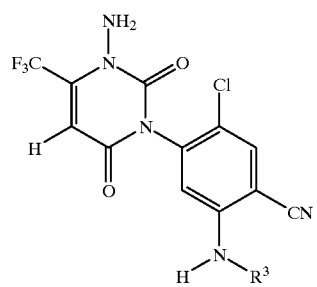

$R^3$ has, for example, the meanings given above for Group 1.

Group 4

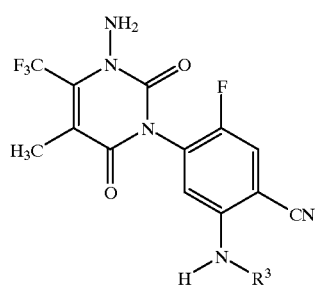

$R^3$ has, for example, the meanings given above for Group 1.

Group 5

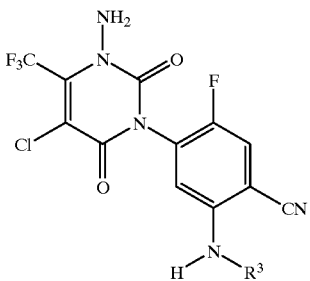

$R^3$ has, for example, the meanings given above for Group 1.

Group 6

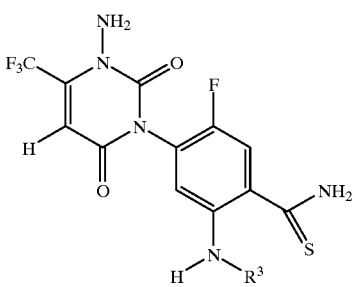

$R^3$ has, for example, the meanings given above for Group 1.

Group 7

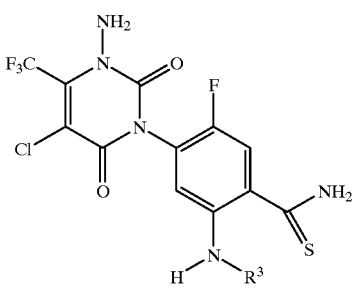

$R^3$ has, for example, the meanings given above for Group 1.

Group 8

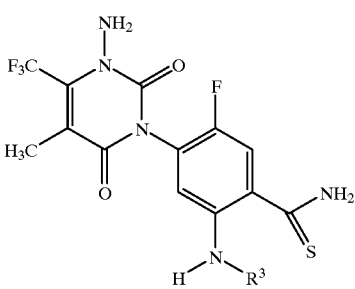

$R^3$ has, for example, the meanings given above for Group 1.

Group 9

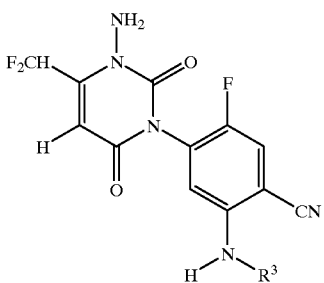

$R^3$ has, for example, the meanings given above for Group 1.

Group 10

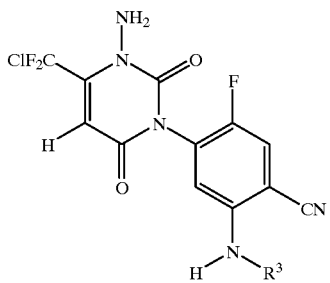

$R^3$ has, for example, the meanings given above for Group 1.

Group 11

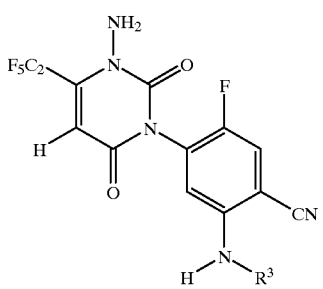

$R^3$ has, for example, the meanings given above for Group 1.

Using, for example, 3-amino-4-chlorodifluoromethyl-1-(4-cyano-2-fluoro-5-methylsulphonylamino-phenyl)-3,6-dihydro-2,6-dioxo-1(2H)-pyrimidine and dichloroacetyl chloride as starting materials, the course of the reaction in the process according to the invention can be illustrated by the following equation:

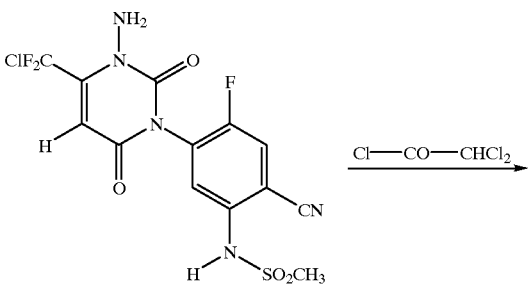

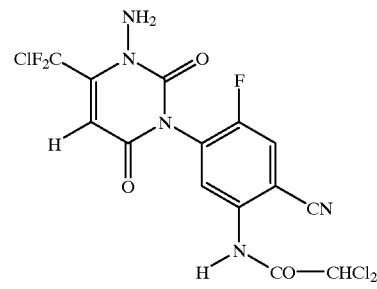

A general definition of the aminouracils to be used as starting materials in the process according to the invention for the preparation of the compounds of the formula (I) is given by the formula (II). In the formula (II), $R^1$, $R^2$, $R^5$, $R^6$, $R^7$ and $R^8$ each preferably or in particular have those meanings which have already been indicated above, in connection with the description of the compounds of the formula (I) to be prepared according to the invention, as being preferable or, respectively, particularly preferable for $R^1$, $R^2$, $R^5$, $R^6$, $R^7$ and $R^8$; Z preferably represents optionally halogen-substituted $C_1$–$C_4$-alkylsulphonylamino, amino or optionally halogen-substituted $C_1$–$C_4$-alkyl-carbonylamino, in particular methylsulphonylamino, ethylsulphonylamino or trifluoroacetylamino.

The starting materials of the formula (II) are known and/or can be prepared by known processes (cf. EP 408382, EP 648749).

A general definition of the alkylating or acylating agents further to be used as starting materials in the process according to the invention for the preparation of the compounds of the formula (I) is given by formulae (III), (IV), (V) and (VI). In these formulae, $R^3$ and $R^4$ each preferably or in particular have those meanings which have already been indicated above, in connection with the description of the compounds of the formula (I) to be prepared according to the invention, as being preferable or, respectively, particularly preferable for $R^3$ and $R^4$.

The starting materials of the formulae (III), (IV), (V) and (VI) are known chemicals for synthesis.

The process according to the invention for preparing compounds of the formula (I) is preferably carried out in the presence of a suitable reaction auxiliary. Suitable reaction auxiliaries are generally the customary inorganic or organic bases or acid acceptors. These include preferably alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate, or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; furthermore also basic organic nitrogen compounds, such as, for example trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), and 1,8 diazabicyclo[5,4,0]-undec-7-ene (DBU).

The process according to the invention for preparing compounds of the formula (I) is preferably carried out in the presence of a diluent. Suitable diluents are in general the customary organic solvents. These include preferably aliphatic, alicyclic and aromatic, optionally halogenated hydrocarbons, such as, for example, pentane, hexane, heptane, petroleum ether, ligroin, benzine, benzene, toluene, xylene, chlorobenzene, dichlorobenzene, cyclohexane, methylcyclohexane, dichloromethane (methylene chloride), trichloromethane (chloroform) or carbon tetrachloride, dialkyl ethers, such as, for example, diethyl ether, diisopropyl ether, methyl t-butyl ether (MTBE), ethyl t-butyl ether, methyl t-pentyl ether (TAME), ethyl t-pentyl ether, tetrahydrofuran (THF), 1,4-dioxane, ethylene glycol dimethyl ether or ethylene glycol diethyl ether, diethylene glycol dimethyl ether or diethylene glycol diethyl ether; dialkyl ketones, such as, for example, acetone, butanone, (methyl ethyl ketone), methyl i-propyl ketone or methyl i-butyl ketone, nitriles, such as, for example, acetonitrile, propionitrile, butyronitrile or benzonitrile; amides, such as, for example, N,N-dimethyl-formamide (DMF), N,N-dimethyl-acetamide, N-methyl-formanilide, N-methyl-pyrrolidone or hexamethyl-phosphoric triamide; esters, such as, for example, methyl acetate, ethyl acetate, n- or i-propyl acetate, n-, i- or s-butyl acetate; sulphoxides, such as, for example, dimethylsulphoxide; alcanols, such as, for example, methanol, ethanol, n- or i-propanol, n-, i-, s- or t-butanol, ethylene glycol monomethyl ether or ethylene glycol monoethyl ether, diethylene glycol monomethyl ether or diethylene glycol monoethyl ether; their mixtures with water or pure water.

In the practice of the process according to the invention, the reaction temperatures can be varied over a relatively wide range. Generally, the reaction is carried out at temperatures between 0° C. and 150° C., preferably between 10° C. and 120° C.

The process according to the invention is generally carried out at atmospheric pressure. However, it is also possible to carry out the process according to the invention under elevated or reduced pressure—generally between 0.1 bar and 10 bar.

In the practice of the process according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred for several hours at the temperature required. Work-up is carried out by conventional methods (cf. the preparation examples).

The active compounds according to the invention can be used as defoliants, desiccants, haulm killers and, especially, as weed-killers. By weeds in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective control of weeds in annual cultures.

The compounds of the formula (I) according to the invention are suitable in particular for selectively controlling monocotyledonous and dicotyledonous weeds in monocotyledonous cultures, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example anilides, such as diflufenican and propanil; arylcarboxylic acids, such as dichloropicolinic acid, dicamba and picloram; aryloxyalkanoic acids, such as 2,4-D, 2,4-DB, 2,4-DP, fluroxypyr, MCPA, MCPP and triclopyr; aryloxy-phenoxy-alkanoic esters, such as diclofop-methyl, fenoxaprop-ethyl, fluazifop-butyl, haloxyfop-methyl and quizalofop-ethyl; azinones, such as chloridazon and norflurazon; carbamates, such as chlorpropham, desmedipham, phenmedipham and propham; chloroacetanilides, such as alachlor, acetochlor, butachlor, metazachlor, metolachlor, pretilachlor and propachlor; dinitroanilines, such as oryzalin, pendimethalin and trifluralin; diphenyl ethers, such as acifluorfen, bifenox, fluoroglycofen, fomesafen, halosafen, lactofen and oxyfluorfen; ureas, such as chlorotoluron, diuron, fluometuron, isoproturon, linuron and methabenzthiazuron; hydroxylamines, such as alloxydim, clethodim, cycloxydim, sethoxydim and tralkoxydim; imidazolinones, such as imazethapyr, imazamethabenz, imazapyr and imazaquin; nitriles, such as bromoxynil, dichlobenil and ioxynil; oxyacetamides, such as mefenacet; sulphonylureas, such as amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as butylate, cycloate, diallate, EPTC, esprocarb, molinate, prosulfocarb, thiobencarb and triallate; triazines, such as atrazine, cyanazine, simazine, simetryne, terbutryne and terbutylazine; triazinones, such as hexazinone, metamitron and metribuzin; and others, such as aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples.

PREPARATION EXAMPLES

Example 1

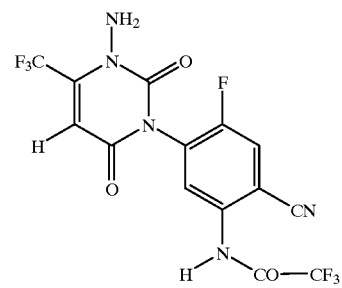

A mixture of 2.1 g (5 mmol) of 3-amino-1-(4-cyano-2-fluoro-5-ethylsulphonyl-amino-phenyl)-5-trifluoromethyl-3,6-dihydro-2,6-dioxo-1(2H)-pyrimidine, 1.1 g (5.5 mmol) of trifluoroacetic anhydride, 1 ml of triethylamine and 20 ml of acetonitrile is heated under reflux for 30 hours and then concentrated using water pump vacuum. The residue is taken up on ethyl acetate, washed with 1N hydrochloric acid, dried with sodium sulphate and filtered. The filtrate is concentrated using water pump vacuum, and the crude product which is obtained as residue is purified by column chromatography (silica gel, chloroform/ethyl acetate, Vol. 1:1).

0.8 g (38% of theory) of 3-amino-1-(4-cyano-2-fluoro-5-trifluoroacetyl-amino-phenyl)-5-trifluoromethyl-3,6-dihydro-2,6-dioxo-1(2H)-pyrimidine is obtained.

$^1$H NMR (dimethyl sulphoxide-D6, δ): 6.47 ppm.

Similar to the method of Example 1 and according to the general description of the process according to the invention, for example the compounds of the formula (I) listed in Table 1 below can also be prepared.

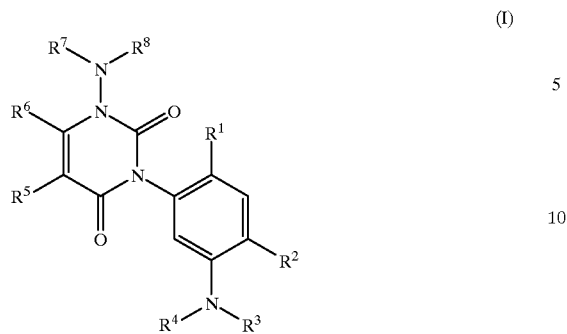

(I)

TABLE 1

Examples of compounds of the formula (I)

| Ex. No. | R¹ | R² | R³ | R⁴ | R⁵ | R⁶ | R⁷ | R⁸ | physical data |
|---|---|---|---|---|---|---|---|---|---|
| 2 | F | CN | H | H | H | CF₃ | H | H | |
| 3 | F | CN | H | CH₃ | H | CF₃ | H | H | |
| 4 | F | CN | CH₃ | CH₃ | H | CF₃ | H | H | |
| 5 | F | CN | CH₃ | C₃H₇-i | H | CF₃ | H | H | |
| 6 | F | CN | H | C₂H₅ | H | CF₃ | H | H | |
| 7 | F | CN | H | C₃H₇-n | H | CF₃ | H | H | |
| 8 | F | CN | H | C₃H₇-i | H | CF₃ | H | H | |
| 9 | F | CN | —(CH₂)₄— | | H | CF₃ | H | H | |
| 10 | F | CN | H | COCF₃ | H | CF₃ | H | H | |
| 11 | F | CN | H | COC₂F₅ | H | CF₃ | H | H | |
| 12 | F | CN | H | COCH₃ | H | CF₃ | H | H | |
| 13 | F | CN | COCH₃ | COCH₃ | H | CF₃ | H | H | |
| 14 | F | CN | —CO—CH₂CH₂—CO— | | H | CF₃ | H | H | |
| 15 | F | CN | H | COC₂H₅ | H | CF₃ | H | H | |
| 16 | F | CN | H | COC₆H₅ | H | CF₃ | H | H | |
| 17 | F | CN | H | CO-(2-thienyl) | H | CF₃ | H | H | |
| 18 | F | CN | H | CO-(2-pyridyl) | H | CF₃ | H | H | |
| 19 | F | CN | H | COC₄H₉-t | H | CF₃ | H | H | |
| 20 | F | CN | H | COC₃H₇-i | H | CF₃ | H | H | |
| 21 | F | CN | CH₃ | COCH₃ | H | CF₃ | H | H | |
| 22 | F | CN | C₂H₅ | COC₄H₉-n | H | CF₃ | H | H | |
| 23 | F | CN | CH₃ | COCF₃ | H | CF₃ | H | H | |
| 24 | F | CN | COCH₃ | CH₂C≡CH | H | CF₃ | H | H | |
| 25 | F | CN | H | CH₂COOCH₃ | H | CF₃ | H | H | |
| 26 | F | CN | CH₃ | CH₂COOCH₃ | H | CF₃ | H | H | |
| 27 | F | CN | COCH₃ | CH₂CN | H | CF₃ | H | H | |

TABLE 1-continued

Examples of compounds of the formula (I)

| Ex. No. | R¹ | R² | R³ | R⁴ | R⁵ | R⁶ | R⁷ | R⁸ | physical data |
|---|---|---|---|---|---|---|---|---|---|
| 28 | F | CN | H | CH₂CH₂CN | H | CF₃ | H | H | |
| 29 | F | CSNH₂ | H | COCF₃ | H | CF₃ | H | H | |
| 30 | F | CN | H | COCHCl₂ | H | CF₃ | H | H | |
| 31 | F | CN | | (CH₂C(O)CH₂C(O)CH₃) | H | CF₃ | H | H | |
| 32 | F | CN | | (CH₂C(O)CH(CF₃)C(O)CH₃) | H | CF₃ | H | H | |
| 33 | F | CN | H | CH₃ | H | CF₃ | CH₃ | H | |
| 34 | F | CSNH₂ | H | CH₃ | H | CF₃ | CH₃ | H | |
| 35 | F | CN | H | (allyl) | H | CF₃ | H | H | |

USE EXAMPLES

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is watered with the preparation of the active compound. Advantageously, the amount of water per unit area is kept constant. The active compound concentration in the preparation is not important, only the active compound application rate per unit area being decisive.

After three weeks, the degree of damage to the plants is rated in % damage in comparison with the development of the untreated control.

The figures denote:

0%=no action (like untreated control)

100%=total destruction

In this test, a very strong activity against weeds such as Setaria (100%), Sorghum (90%), Abutilon (100%), Galium (100%), Matricaria (100%) and Polygonum (100%) is shown, for example, by the compound of Preparation Example 1 at an application rate of 30 g/ha, combined with very good tolerance by crops, such as, for example, maize (0%).

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the amounts of active compound desired are applied in 1000 l/ha.

After three weeks, the degree of damage to the plants is rated in % damage in comparison with the development of the untreated control.

The figures denote:

0%=no action (like untreated control)

100%=total destruction

In this test, a very strong activity against weeds such as Echinochloa (100%), Abutilon (100%), Datura (100%), Ipomoea (100%) and Viola (100%) is shown, for example, by the compound of Preparation Example 1 at an application rate of 30 g/ha, combined with very good tolerance by crops, such as, for example, wheat (0%).

We claim:

1. Substituted aminouracils of the formula (I)

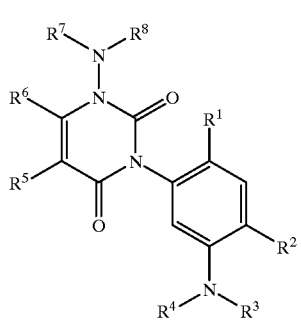

(I)

in which the substituents R¹, R², R³, R⁴, R⁵, R⁶, R⁷ and R⁸ represent the following:

| R¹ | R² | R³ | R⁴ | R⁵ | R⁶ | R⁷ | R⁸ |
|---|---|---|---|---|---|---|---|
| F | CN | H | H | H | CF₃ | H | H |
| F | CN | H | CH₃ | H | CF₃ | H | H |

-continued

| R¹ | R² | R³ | R⁴ | R⁵ | R⁶ | R⁷ | R⁸ |
|---|---|---|---|---|---|---|---|
| F | CN | CH³ | CH₃ | H | CF₃ | H | H |
| F | CN | CH₃ | C₃H₇-i | H | CF₃ | H | H |
| F | CN | H | C₂H₅ | H | CF₃ | H | H |
| F | CN | H | C₃H₇-n | H | CF₃ | H | H |
| F | CN | H | C₃H₇-i | H | CF₃ | H | H |
| F | CN | —(CH₂)₄— | | H | CF₃ | H | H |
| F | CN | H | COCF₃ | H | CF₃ | H | H |
| F | CN | H | COC₂F₅ | H | CF₃ | H | H |
| F | CN | H | COCH₃ | H | CF₃ | H | H |
| F | CN | COCH₃ | COCH₃ | H | CF₃ | H | H |
| F | CN | —CO—CH₂CH₂—CO— | | H | CF₃ | H | H |
| F | CN | H | COC₂H₅ | H | CF₃ | H | H |
| F | CN | H | COC₆H₅ (phenacyl) | H | CF₃ | H | H |
| F | CN | H | CO-(2-thienyl) | H | CF₃ | H | H |
| F | CN | H | CO-(2-pyridyl) | H | CF₃ | H | H |
| F | CN | H | COC₄H₉-t | H | CF₃ | H | H |
| F | CN | H | COC₃H₇-i | H | CF₃ | H | H |
| F | CN | CH₃ | COCH₃ | H | CF₃ | H | H |
| F | CN | C₂H₅ | COC₄H₉-n | H | CF₃ | H | H |
| F | CN | CH₃ | COCF₃ | H | CF₃ | H | H |
| F | CN | COCH₃ | CH₂C≡CH | H | CF₃ | H | H |
| F | CN | H | CH₂COOCH₃ | H | CF₃ | H | H |
| F | CN | CH₃ | CH₂COOCH₃ | H | CF₃ | H | H |
| F | CN | COCH₃ | CH₂CN | H | CF₃ | H | H |
| F | CN | H | CH₂CH₂CN | H | CF₃ | H | H |
| F | CSNH₂ | H | COCF₃ | H | CF₃ | H | H |
| F | CN | H | COCHCl₂ | H | CF₃ | H | H |
| F | CN | CH₃COCH₂CH₂COCH₃ (diketone) | | H | CF³ | H | H |
| F | CN | CH₃COCH(CF₃)COCH₃ | | H | CF₃ | H | H |
| F | CN | H | CH₃ | H | CF₃ | CH₃ | H |
| F | CSNH₂ | H | CH₃ | H | CF₃ | CH₃ | H |
| F | CN | H | CH₂CH₂CH=CH₂ | H | CF₃ | H | H |

2. A substituted aminouracil of the formula

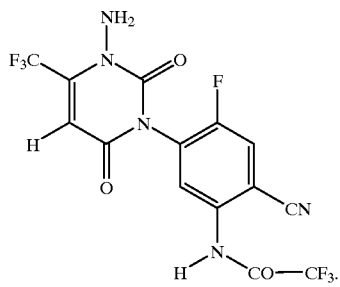

3. Herbicidal compositions, comprising at least one substituted aminouracil of the formula (I) according to claim 1 and an extender or surface active substance.

4. A method for controlling undesirable plants, comprising administering to such plants or to a locus from which it is desired to exclude such plants an herbicically effective amount of substituted aminouracils of the general formula (I) according to claim 1.

* * * * *